United States Patent [19]

Fannin et al.

[11] 4,222,969
[45] Sep. 16, 1980

[54] HYDROCARBON SOLUBLE MAGNESIUM COMPOSITIONS OF HIGH MAGNESIUM CONTENT

[75] Inventors: Loyd W. Fannin, Dickinson; Dennis B. Malpass, LaPorte, both of Tex.

[73] Assignee: Texas Alkyls, Inc., Deer Park, Tex.

[21] Appl. No.: 27,205

[22] Filed: Apr. 5, 1979

Related U.S. Application Data

[63] Continuation-in-part of Ser. No. 945,665, Sep. 25, 1978, abandoned.

[51] Int. Cl.³ .............................................. C07F 3/02
[52] U.S. Cl. .............................................. 260/665 R
[58] Field of Search .................................. 260/665 R

[56] References Cited

U.S. PATENT DOCUMENTS

| | | | |
|---|---|---|---|
| 3,264,360 | 8/1966 | Nudenberg et al. | 260/665 R |
| 3,450,683 | 6/1969 | Hsich et al. | 252/431 R X |
| 3,646,231 | 2/1972 | Kamienski et al. | 260/665 R |
| 3,704,287 | 11/1972 | Johnson | 252/431 R X |
| 3,737,393 | 6/1973 | de Vries | 252/431 R |
| 3,766,280 | 10/1973 | Kamienski et al. | 260/665 R |
| 4,069,267 | 1/1978 | Kamienski et al. | 260/665 R |
| 4,127,507 | 11/1978 | Fannin et al. | 260/665 R X |

FOREIGN PATENT DOCUMENTS 1251177 10/1971 United Kingdom .

OTHER PUBLICATIONS

Chemical Abstracts 88, 170793v, (1978).
Chemical Abstracts 88, 170794w (1978).

*Primary Examiner*—Helen M. S. Sneed
*Attorney, Agent, or Firm*—M. Henry Heines

[57] ABSTRACT

A composition of matter comprising di-n-butylmagnesium and dimethylmagnesium, to the exclusion of dialkylmagnesium compounds containing alkyl groups other than n-butyl or methyl, with an n-butyl:methyl alkyl group ratio of about 0.2:1 to about 5:1 which is soluble in aliphatic, cycloaliphatic, and aromatic hydrocarbon solvents is disclosed. The composition is prepared in the substantial absence of oxygen and moisture by the simultaneous or consecutive reactions of methyl and n-butyl halides with metallic magnesium in the presence of the hydrocarbon solvent, followed by separation of the insoluble magnesium chloride and any unreacted magnesium metal from the resulting solution.

21 Claims, No Drawings

HYDROCARBON SOLUBLE MAGNESIUM COMPOSITIONS OF HIGH MAGNESIUM CONTENT

CROSS REFERENCE TO RELATED APPLICATIONS

This is a continuation-in-part of U.S. patent application Ser. No. 945,665, filed Sept. 25, 1978 abandoned.

BACKGROUND OF THE INVENTION

Diorganomagnesium compounds are well known for their usefulness in a wide variety of chemical reactions. As reagents, these compounds can be used for the reduction of ketones, the metalation of aromatic compounds, and the alkylation of metal halides or oxides to the corresponding metal alkyls. As catalysts, diorganomagnesium compounds are useful in the dimerization and polymerization of olefins, see Brit. Pat. No. 1,251,177, the polymerization of epoxides, see U.S. Pat. No. 3,444,102, and the preparation of telomers, see U.S. Pat. No. 3,742,077. While they perform many of the same types of functions performed by Grignard reagents, diorganomagnesium compounds, owing to differences in electronic and steric factors, are more reactive than Grignard reagents toward certain types of compounds. In general, see also U.S. Pat. Nos. 3,646,231 and 3,822,219.

The utility of diorganomagnesium compounds is lessened by the fact that many are either solids or highly viscous liquids and all are unstable upon exposure to moisture and air. This problem is generally overcome either by dissolving the compound in an inert hydrocarbon solvent or by solvating the compound and by handling under an inert atmosphere. Many diorganomangesium compounds, particularly those with straight chain lower alkyl groups with a chain length of up to four carbon atoms, are insoluble by themselves in hydrocarbon solvents and thus require solubilizing agents which will form a soluble complex. Examples of such solubilizing agents are alkyllithium compounds, see U.S. Pat. No. 3,742,077, dialkyl zinc compounds, see U.S. Pat. No. 3,444,102, alkali metal hydrides, see U.S. Pat. No. 3,655,790, and organoaluminum compounds, see U.S. Pat. Nos. 3,737,393 and 3,028,319.

Solvation involves the use of an ether or an organic base molecule to associate directly with the magnesium atom, thus rendering a liquid-phase complex. The solvated form is undesirable, however, since solvation seriously inhibits the effectiveness of the compound, particularly when the compound is used as a Ziegler-type catalyst. The use of ether is particularly undesirable due to considerations of flammability and explosibility, and because it introduces soluble RMgX according to the Schlenk equilibrium

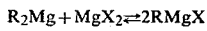

where R is alkyl and X is halogen.

Solubilization also serves to reduce the viscosity of reaction mixtures whose high viscosity would otherwise inhibit the progress of the reaction and cause difficulty in handling and transferring. This problem is only partially solved by the use of chloroaryl solvents to form low viscosity suspensions of the insoluble compounds, as described in U.S. Pat. No. 3,264,360.

In addition, the insolubility of the lower alkyl magnesium compounds makes preparation of them in a form free of undesirable halides difficult. In particular, the direct reaction of magnesium metal with an organic halide is disclosed in Glaze and Selman, *Journal of Organometallic Chemistry*, Vol. 5, p. 477 (1967), and W. N. Smith, *Journal of Organometallic Chemistry*, Vol. 64, p. 25 (1974). These articles deal with the preparation of diorganomagnesium compounds with straight chain alkyl groups of 5 carbon atoms and higher. Such compounds are soluble in hydrocarbon solvents and thus readily separable from the concurrently produced magnesium halide and unreacted magnesium. When lower straight chain alkyls are used in this process, the desired diorganomagnesium compound is formed but is insoluble and exists as a slurry in the solvent together with the magnesium halide and unreacted magnesium metal. Thus a solubilizing agent is required when this process is used to make lower alkyl diorganomagnesium compounds. The latter are particularly desirable as reagents and catalysts owing to their relatively high magnesium content on a weight basis.

Other methods of preparation include the mercury-magnesium exchange method, as disclosed in Cowan and Mosher, *Journal of Organic Chemistry*, Vol. 27, p. 1 (1962), and the dioxanate-precipitation method, as disclosed in Schlenk, *Berichte der Deutschen Chemischen Gesellschaft*, Vol. 64, p. 734 (1931). The mercury method,

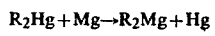

where R is alkyl, is limited by the high cost of dialkylmercury compounds, and the health hazards involved in their use. The reaction itself is hazardous since it proceeds rapidly and exothermically after an inhibition period.

The dioxanate-precipitation method,

where R is alkyl and X is halogen, involves removal of magnesium halide from ether solutions of Grignard reagents by precipitation of a complex which the dioxane forms with the halide. This is a tedious process and results in an etherated dialkylmagnesium complex from which the ether must be removed prior to use as a catalyst.

Dialkylmagnesiums can also be prepared from alkyllithiums, see U.S. Pat. No. 3,646,231, by precipitation of lithium halide,

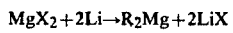

where R is alkyl and X is halogen. This process is unsuitable for straight-chain lower alkyl diorganomagnesiums which are insoluble in hydrocarbon solvents, since separation will be impossible. The use of basic solvents renders separation possible but requires subsequent desolvation. This reference also discloses the use of a hydrocarbon-soluble diorganomagnesium to solubilize an insoluble diorganomagnesium. The solubilizing members shown in this reference, however, invariably contain branched chain alkyl groups. Such branched chain diorganomagnesium compounds cannot be prepared by the Glaze and Selman method mentioned above. This fact is established in the work of Kamienski and Eastham, *Journal of Organic Chemistry*, Vol. 34, p. 1116 (1968). Thus, resort to the lithium halide precipitation method is required. The use of two individually insoluble straight chain diorganomagnesium compounds to mutually solubilize each other has not been disclosed, particularly two such compounds which can be prepared by the direct reaction between magnesium metal and alkyl halide.

The general insolubility of straight chain lower alkyl magnesium compounds is thought to be due to intermolecular association resulting in the formation of a polymer-type macro-structure wherein each magnesium atom is tetrahedrally surrounded by four alkyl groups. Known methods of solubilizing these compounds presumably operate to break some of the intermolecular bonds and thereby break down the macro-structure into smaller units. Solvation or complexing as described above are thought to bring about this effect.

Alkylmagnesium compounds containing either branched chain alkyl groups or straight chain alkyl groups of five carbon atoms or more, known to be effective as solubilizing agents, are also thought to operate by breaking the intermolecular bonds. With alkylmagnesium compounds, however, the effect is thought to occur by way of alkyl interchange and re-association, whereby the solubilizing alkyl groups exchange positions with some of the straight chain lower alkyls. Polymerization is thus sterically hindered, either because the substituted groups are unwieldy for a tetrahedral fit around the magnesium atom, or because the groups have some inherent solubility of their own.

Thus, it is surprising that two independently insoluble and presumably polymer-forming dialkylmagnesium compounds can solubilize each other. Stated differently, it is surprising and unexpected that alkyl interchange between di-n-butylmagnesium and dimethylmagnesium is sufficient to break down the intermolecular bonds and render a soluble mixture. Consistent with the alkyl-interchange theory, equimolar combinations of di-n-butylmagnesium and dimethylmagnesium are considered equivalent to n-butylmethylmagnesium. This theory is offered merely to show the unexpected nature of the composition of the present invention, and is intended neither to define nor to limit the invention in any manner.

It is therefore an object of the present invention to provide hydrocarbon-soluble diorganomagnesium compositions of high magnesium content.

A further object of the present invention is to provide a process by which hydrocarbon soluble diorganomagnesium compositions of high magnesium content can be prepared by the direct reaction of alkyl halides with magnesium.

A still further object of the present invention is to provide a means for solubilizing straight chain lower alkyl diorganomagnesium compounds in hydrocarbon solvents.

Another object of the present invention is to provide a composition of matter comprising di-n-butylmagnesium, dimethylmagnesium, and a hydrocarbon solvent.

Yet another object of the present invention is to provide a process for the manufacture of halide-free, metallic magnesium-free, and unsolvated straight-chain, lower alkyl diorganomagnesium compounds using raw materials which are less expensive than those required for existing processes.

BRIEF DESCRIPTION OF THE INVENTION

The present invention relates to the discovery that a composition of matter comprising di-n-butylmagnesium and dimethylmagnesium is soluble in hydrocarbon solvents. While neither of these two compounds is soluble alone, each has the effect of rendering the other soluble. The composition of this invention optionally contains other components such as solvents, viscosity reducers, cocatalysts, etc., to the exclusion, however, of dialkylmagnesium compounds containing alkyl groups other than n-butyl or methyl. Related to this discovery is the further discovery that a hydrocarbon-soluble mixture of these two compounds can be prepared by direct reaction between metallic magnesium and each of the two corresponding alkyl halides added in consecutive manner to the same vessel. This discovery is in contrast to the known behavior of these compounds, in that when similarly prepared in separate vessels, the compounds are insoluble and thus inseparable from both the concurrently formed magnesium halide and any unreacted magnesium metal remaining in the vessel. The present invention thus provides a novel method for the preparation of straight-chain lower alkyl diorganomagnesium compounds in hydrocarbon solution substantially free of halides and metallic magnesium without the use of solubilizing agents or solvation.

DETAILED DESCRIPTION OF THE INVENTION

According to the present invention, di-n-butyl magnesium and dimethylmagnesium are combined to provide a composition which is soluble in hydrocarbon solvents.

The term "hydrocarbon solvent" is used herein to designate aliphatic, cycloaliphatic, and aromatic hydrocarbons. Illustrative of aliphatic solvents are n-pentane, isopentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and α-methylnaphthalene. Preferred solvents are those containing 5 to 20 carbon atoms, inclusive. More preferred are those containing 6 to 15 carbon atoms, inclusive. Particularly preferred solvents are those which have boiling points between about 69° C. and about 110° C.

The concentration of dialkylmagnesium in the solvent is not critical and the compounds are soluble over a wide range of concentration. The solution viscosity increases with concentration, however. For greater ease of handling, therefore, the dialkylmagnesium concentration is normally from about 0.2 to about 12.0 weight percent, preferably from about 1.0 to about 5.0 weight percent in terms of magnesium.

The solution can be prepared by physically combining the two solid dialkylmagnesium compounds with the hydrocarbon solvent. A clear solution results which is readily separable from any insolubles retained with the compounds. Thus, di-n-butylmagnesium, as a solid or slurry, existing in admixture with magnesium halides, lithium halides, other insoluble by-products of the manufacturing process, or unreacted starting materials, can be contacted with a hydrocarbon solvent in the presence of dimethylmagnesium, or vice versa, to produce a solution containing the two as solutes, substantially free of the others. Solubilization can be hastened by heating the solution to a temperature of about 50° C. or higher. The rate of solubilization increases as the temperature is raised. Once the compounds are dissolved, they will remain in solution upon any subsequent lowering of temperature.

If desired, separation of the solution from the remaining undissolved solids can be enhanced by the use of any of the variety of viscosity reducing agents known in the art. Examples of such viscosity reducing agents are organoaluminum compounds such as trialkylaluminums, dialkylaluminum halides, and alkylaluminum dihalides.

Alternatively, di-n-butylmagnesium and dimethylmagnesium can be prepared directly in the solvent in a common vessel by either simultaneous or subsequent reactions. Any reaction is suitable in which neither the by-products nor the unreacted starting materials are soluble in the final mixture. The insolubles can thus be easily filtered off. One such technique involves the direct reaction between metallic magnesium and n-butyl and methyl halides. The concurrently produced magnesium chloride forms a precipitate which is readily removed from the solution together with any unreacted magnesium still present. Another technique involves the use of a Grignard reagent, preferably methyl magnesium chloride, to supply the methyl group. The Grignard reagent is preferably freed of all ether used in its preparation prior to its use in the present reaction. The desired solution of n-butyl and methyl magnesium compounds is then obtained by reaction of the desolvated methyl Grignard reagent with the reaction product of an n-butyl halide with magnesium metal.

Following any of the above procedures, the solids can be removed from the reaction mixture by any conventional technique, for example, centrifuging, decanting, or filtration. The resulting solution of di-n-butylmagnesium and dimethylmagnesium can then be diluted or concentrated to give the concentration desired for purposes of reactivity, viscosity, or economic considerations.

The mutual solubilizing effect is achieved at n-butyl:methyl mole ratios of from about 0.2:1 to about 5:1. The preferred range of mole ratio is from about 0.5:1 to about 4:1, with the most preferred range being from about 1:1 to about 2:1. Generally, the mutual solubilizing effect is not complete and a quantity of either or both of the two compounds remains undissolved.

When magnesium is reacted directly with an alkyl halide, commercial grade magnesium turnings or shavings can be used. It is preferable, however, to use a form of magnesium with a higher surface area than either of the above. This can be accomplished by milling, but it is most preferable to use the metal in a finely divided state, for instance, as a powder with a particle size equal to or less than about 150 microns.

When the magnesium/methyl halide reaction and the magnesium/n-butyl halide reaction are done in a common vessel, it is preferable to do the methyl halide reaction first. Since methyl halides are more stable than n-butyl halides, they react with magnesium at a slower rate and provide improved control when added first. In fact, a magnesium activating agent is normally required to initiate the methyl halide reaction. The term "magnesium activating agent" is used herein to denote heat or any substance which, when contacted with magnesium, will cause the magnesium to react with the methyl halide at a substantially faster rate. Many activating agents are known in the art. Typical examples are $AlCl_3$, $AlCl_3$-ether complexes, N,N-dimethylaniline, molecular iodine, alkyl halides of at least 3 carbon atoms, and Grignard reagents. Thus, a small quantity of n-butyl halide itself can serve as an activating agent.

Thermal activation is the preferred method and is generally achieved at temperatures between about 125° C. and about 350° C., preferably from about 150° C., to about 250° C., and most preferably from about 150° C. to about 200° C. Once the magnesium is activated, the magnesium/methyl halide reaction can proceed at lower temperatures. Although reaction can occur over a wide temperature range once the magnesium is activated, it will be most convenient to operate between about 20° C. and about 200° C., preferably between about 50° C. and about 175° C., and most preferably between about 100° C. and about 150° C. At least 10% by weight of alkyl halide based on the weight of magnesium metal must be present during thermal activation.

The n-butyl halide reaction is also operable over a wide temperature range, but is most conveniently run at a temperature between about 20° C. and about 200° C., preferably between about 60° C. and about 100° C.

The temperature ranges quoted above are not critical to either reaction. The minimum temperature is dictated largely by process economics, while the maximum temperature is limited only by the possibility of alkyl halide decomposition and consideration of energy conservation.

Although it is preferable to perform the methyl halide reaction first, followed by the n-butyl halide reaction, the reverse order can also be used. When the n-butyl halide reaction is performed first, care must be taken to avoid or eliminate the coating of unreacted magnesium metal with solid di-n-butylmagnesium. Such coating can hinder the subsequent methyl halide reaction by preventing contact between the methyl halide and the magnesium. This problem can be avoided by the use of a large amount of solvent, extra agitation, a slow rate of addition of n-butyl halide, or the addition of excess magnesium. As indicated above, the n-butyl halide can also be used as a magnesium activator for the methyl chloride reaction if a small amount is used, with the remainder added after the methyl halide reaction is completed.

The term "halide" as used herein denotes chloride, bromide, or iodide, or combinations thereof. Chlorides are generally preferred for reasons of economy.

The reactant mole ratio can be varied over a wide range. No particular range is critical to the performance of either of the two reactions. Normally, however, the starting materials will be such that the mole ratio of magnesium to total halides is from about 1.0 to about 2.0, preferably from about 1.1 to about 1.3. The excess magnesium inherent in mole ratios greater than 1.0 is effective in minimizing Wurtz coupling reactions.

The hydrocarbon solvent may be added before, during, or after the reaction. It will be most convenient to add the solvent prior to or during the methyl halide reaction, so that further reaction is less inhibited by high viscosity.

Magnesium alkyls are pyrophoric substances, capable of spontaneous ignition upon contact with air. To prevent such ignition, and also to prevent oxidation of the metallic magnesium, the reactions must be carried out in the absence of more than trace amounts of oxygen. Thus, the reactions are normally carried out in an atmosphere of inert gas such as nitrogen or argon, or in an atmosphere of methyl halide gas. The reactions must also be conducted in the substantial absence of water, due to the susceptibility of the system components to decomposition in the presence of water.

The pressure under which the reactions are conducted is not critical and pressures ranging from atmospheric to elevated pressures of several atmospheres can be employed. The methyl halide reaction will be most conveniently run at least in slight excess of atmospheric in order to keep the methyl halide in solution. The preferred pressure range is about 8 psig ($1.6 \times 10^5$ pascals) to about 100 psig ($8.0 \times 10^5$ pascals). Lower pressures can be used with the n-butyl halide reaction.

The present invention is further illustrated by the following examples.

EXAMPLE 1

This example illustrates the preparation of a heptane solution of di-n-butylmagnesium and dimethylmagnesium. The procedure features the reaction of methyl chloride with metallic magnesium activated by a small amount of n-butyl chloride, followed by the reaction of the remaining magnesium with a larger amount of n-butyl chloride, as follows:

An aerosol compatibility test bottle reactor was charged with 13.0 grams (g) (0.53 g-atom) of 100-mesh magnesium powder and placed in an oil heating bath at 120° C. overnight under a nitrogen purge. The bottle was then evacuated and cooled to 85° C., whereupon 1.5 g of n-butyl chloride was added. A temperature increase of 5° C. was observed, indicating that activation of the magnesium had occurred.

Two hundred grams of heptane was then added to the bottle and the temperature was increased to 100° C. Gaseous methyl chloride was then added below the liquid surface over a four-hour period at 90°-100° C. The quantity of methyl chloride thus added was 10.3 g (0.204 mole). Addition of n-butyl chloride was then begun in the same manner, proceeding for one hour. The total n-butyl chloride charge, including the initial 1.5 g, was 16.6 g (0.179 mole). The reactor was then heated to 145° C. for an additional hour.

Analysis of the viscous solution after centifuging solid fines showed 1.16 weight percent magnesium, corresponding to a yield of 53% of theory. The solution was then hydrolyzed to determine the relative amounts of methyl and n-butyl groups. The hydrolysis gas contained 16.5 mole percent methane and 80.2 mole percent n-butane.

EXAMPLE 2

This example illustrates an alternative preparation of a heptane solution of di-n-butylmagnesium and dimethylmagnesium, involving the use of a Grignard reagent as an intermediate.

A reaction flask was charged with 20 g (0.82 g-atom), of 100-mesh magnesium powder and 36 g of diethyl ether. An ether solution of methyl chloride (9.5 g, 0.19 mole) was slowly added at reflux temperature. During the addition, a considerable amount of methyl chloride escaped through the condenser, leaving only 0.014 g-atom of magnesium dissolved in the reaction flask in the form of methyl magnesium chloride. The latter was subsequently stripped of ether by heating to 195° C. for 30 minutes. A sample of the hydrolyzate was analyzed by gas chromatography for ether content, and none was detected.

The temperature of the flask was then lowered to 90° C. and 20 g of heptane was added. The slurry was then heated to reflux and 1.0 g (0.011 mole) of n-butyl chloride was slowly added. A viscous solution resulted, containing 0.93 weight percent magnesium and 0.10 weight percent chloride (yield indeterminate due to initial methyl chloride loss, see preceding paragraph). The solution was then hydrolyzed to produce a hydrolysis gas containing 30 mole percent methane and 70 mole percent n-butane.

The next three examples are offered to show the unobvious nature of the present invention. In each of these examples, an alkyl group combination was prepared in a manner similar to that described in Example 1 above. Each combination consists of two different alkyl groups, each group containing three carbon atoms or less. The fact that none of the combinations is soluble in heptane demonstrates the unobvious nature of the soluble methyl-n-butyl combination.

EXAMPLE 3 n-Propyl/n-Butyl Combination

The pressure bottle described in Example 1 was purged with nitrogen and charged with 11.0 g (0.45 g-atom) of magnesium powder. The bottle and its contents were then heated to 93° C. and a small amount of n-propyl chloride was added. As indicated above in the specification, alkyl halides of three carbon atoms or higher are self-initiating in their reaction with magnesium powder. Thus, no further magnesium activating agent was required.

The bottle was cooled and 170 g of heptane was added. The bottle and its contents were then heated to 97° C. and additional n-propyl chloride was added in increments to bring the total charge to 13.0 g (0.165 mole) of n-propyl chloride. n-Butyl chloride was then fed in increments to a total n-butyl chloride charge of 13.2 g (0.143 mole). The temperature was then maintained for an additional two hours.

Upon subsequent cooling, the hydrocarbon phase was analyzed for its magnesium content, and only 0.01 weight percent magnesium could be detected, corresponding to less than 1% theoretical yield. The reaction products were thus essentially insoluble.

To confirm the insolubility of the reaction products, 9.6 g of triethylaluminum (a well-known solubilizing agent) was added to the product slurry and the reaction bottle was heated to 80° C. Analysis of the resulting solution showed 1.30 weight percent magnesium, corresponding to 73% theoretical yield, with approximately equimolar amounts of n-propane and n-butane in the hydrolysis gas.

EXAMPLE 4

Ethyl/n-Propyl Combination

With the same procedure and approximately the same molar quantities shown in Example 3 above, a mixture of diethylmagnesium and di-n-propylmagnesium was prepared. Analysis of the hydrocarbon phase indicated only 0.07 weight percent magnesium in soluble form, corresponding to approximately 3.5% theoretical yield.

Trimethylaluminum, another well-known solubilizing agent, was added to induce solubilization of the system components. Analysis of the resulting solution indicated 1.60% soluble magnesium, or 80% theoretical yield, with approximately equimolar amounts of ethane and n-propane in the hydrolysis gas.

EXAMPLE 5

Methyl/Ethyl Combination

The pressure bottle described in Example 1 was purged with nitrogen and charged with 13.0 g (0.53 g-atom) of magnesium powder. A small amount (0.24 g) of di-n-hexylmagnesium was added to activate the metal together with 184 g of heptane, and the bottle was heated to 100°–110° C. While this temperature was maintained, 13.3 g (0.21 mole) of ethyl chloride was added slowly over a period of two hours.

Following the ethyl chloride addition, the system temperature was raised to 130°–136° C. and methyl chloride was added in a quantity of 6.6 g (0.13 mole) over a period of two hours. The reaction mixture was then held at 130° C. for six hours.

The solids in the reaction mixture were then allowed to settle and the clear hydrocarbon phase was sampled. Analysis of the sample indicated only 0.03 weight percent magnesium, or about 1.5% theoretical yield.

As in Examples 3 and 4, the solids were then solubilized by the addition of tri-n-octylaluminum. Analysis of the resulting solution indicated 0.83 weight percent magnesium, or about 40% yield, with a methane:ethane mole ratio of 0.31:1 in the hydrolysis gas, indicating that both dimethylmagnesium and diethylmagnesium had been made as an insoluble mixture.

What is claimed is:

1. A hydrocarbon-soluble composition of matter comprising di-n-butylmagnesium and dimethylmagnesium at a n-butyl:methyl alkyl group ratio of from about 0.2:1 to about 5:1, to the exclusion of dialkylmagnesium compounds containing alkyl groups other than n-butyl or methyl.

2. A composition according to claim 1 in which the n-butyl:methyl alkyl group ratio is from about 0.5:1 to about 4:1.

3. A composition according to claim 1 in which the n-butyl:methyl alkyl group ratio is from about 1:1 to about 2:1.

4. A process for the manufacture of a hydrocarbon solution of a dialkylmagnesium composition comprising
   (a) reacting, in the presence of a hydrocarbon solvent, magnesium metal with a member selected from the group consisting of a methyl halide in the presence of a magnesium activating agent, and a n-butyl halide,
   (b) either simultaneous to step (a) or subsequent thereto, reacting, in the presence of the solvent of step (a), the unselected member of the group of step (a) with further magnesium metal, to form a mixture of a hydrocarbon solution of a dialkylmagnesium composition and undissolved solids, and
   (c) separating the hydrocarbon solution from the undissolved solids, all steps being conducted in the substantial absence of both moisture and oxygen.

5. The process of claim 4 in which the hydrocarbon solvent is a member selected from the group consisting of aliphatic, cycloaliphatic, and aromatic hydrocarbons containing 5 to 20 carbon atoms, inclusive.

6. The process of claim 4 in which the hydrocarbon solvent is a member selected from the group consisting of aliphatic, cycloaliphatic and aromatic hydrocarbons containing 6 to 15 carbon atoms, inclusive.

7. The process of claim 4 in which the hydrocarbon solvent is a member selected from the group consisting of aliphatic, cycloaliphatic, and aromatic hydrocarbons which have boiling points between about 69° C. and about 110° C.

8. The process of claim 4 in which the magnesium metal is in the powdered state.

9. The process of claim 4 in which the magnesium metal is comprised of particles of diameter equal to or less than about 150 microns.

10. The process of claim 4 in which the magnesium metal of step (a) is reacted with a methyl halide in the presence of a magnesium activating agent.

11. The process of claim 10 in which the magnesium of step (a) is thermally activated at a temperature between about 125° C. and about 350° C.

12. The process of claim 4 in which the mole ratio of magnesium to total halides is between about 1.0 and about 2.0.

13. The process of claim 4 in which the mole ratio of magnesium to total halides is between about 1.1 and about 1.3.

14. The process of claim 4 in which the methyl halide is methyl chloride and the n-butyl halide is n-butyl chloride.

15. A composition of matter comprising the components
   (a) di-n-butylmagnesium,
   (b) dimethylmagnesium, and
   (c) a solvent selected from the group consisting of aliphatic, cycloaliphatic and aromatic hydrocarbons containing 5 to 20 carbon atoms, inclusive,
components (a) and (b) being present in quantities relative to each other such that the n-butyl:methyl mole ratio is between about 0.2:1 and about 5:1, to the exclusion of dialkylmagnesium compounds containing alkyl groups other than n-butyl or methyl.

16. A composition according to claim 15 in which the solvent is a member selected from the group consisting of aliphatic, cycloaliphatic, and aromatic hydrocarbons containing 6 to 15 carbon atoms, inclusive.

17. A composition according to claim 15 in which the solvent is a member selected from the group consisting of aliphatic, cycloaliphatic, and aromatic hydrocarbons which have boiling points between about 69° C. and about 110° C.

18. A composition according to claim 15 in which the concentration of dialkylmagnesium in the solvent is from about 0.2 weight percent to about 12 weight percent in terms of magnesium.

19. A composition according to claim 15 in which the concentration of dialkylmagnesium in the solvent is from about 1 weight percent to about 5 weight percent in terms of magnesium.

20. A composition according to claim 15 in which the n-butyl:methyl alkyl group ratio is from about 0.5:1 to about 4:1.

21. A composition according to claim 15 in which the n-butyl:methyl alkyl group ratio is from about 1:1 to about 2:1.

* * * * *